United States Patent [19]

VandenBerg

[11] Patent Number: Plant 7,386

[45] Date of Patent: Nov. 27, 1990

[54] CHRYSANTHEMUM PLANT NAMED YELLOW TARA

[75] Inventor: Cornelis P. VandenBerg, Salinas, Calif.

[73] Assignee: Yoder Brothers, Inc., Barberton, Ohio

[21] Appl. No.: 389,320

[22] Filed: Aug. 2, 1989

[51] Int. Cl.[5] ..... A01H 5/00

[52] U.S. Cl. ..... Plt./74

[58] Field of Search ..... Plt./74

[56] References Cited

U.S. PATENT DOCUMENTS

P.P. 6,313 9/1988 VandenBerg ..... Plt. 74

OTHER PUBLICATIONS

Gosling, S. G. (Ed.), "Appendix II", *The Chrysanthemum Manual,* Essex Telegraph Press, Ltd. Colchester, U.K., 1979, pp. 329, 330.

Searle, S. A. et al., "Use of Gamma and X-Rays", *Chrysanthemums The Year Round,* Bladford Press, London, U.K., 1968, pp. 27-29.

Broertjes, C., "Mutation Breeding of Chrysanthemums", *Ephytica,* 15 (1966): 156-162, Association EURATOM-ITAL, Wageningen.

Chan, A. P., "Chrysanthemum and Rose Mutations Induced by X Rays", Reprinted from Proceedings of the American Society for Horticultural Science, vol. 88, 1966, Plant Research Institute, Research Branch, Canada Dept. of Agriculture, Ottawa, Canada, pp. 613-620.

Broertjes, C. and A. M. Van Harten, *Application of Mutation Breeding Methods in the Improvement of Vegetatively Propagated Crops,* "Chrysanthemum", Elsevier Scientific Publishing Company, Amsterdam-Oxford-New York, 1978, pp. 162-175.

Broertjes, C., P. Koene and J. W. H. Van Veen, "A Mutant of a Mutant of a Mutant of a . . . Irradiation of Progressive Radiation-Induced Mutants in a Mutation-Breeding Programme with *Chrysanthemum morifolium* Ram.", *Euphytica,* 29 (1980): 525-530.

Teynor, Tim M., Peter D. Ascher, R. E. Widmer and J. J. Luby, "Inheritance of Flower Color in *Dendranthema grandiflora* Tzevelev. (*Chrysanthemum morifolium* Ramat.) Using Cultivars and Inbreds. I. Plastid Pigmentation", *Euphytica,* 42 (1989): 199-207, Kluwer Academic Publishers, Netherlands.

Teynor, Tim M., Peter D. Ascher, R. E. Widmer and J. J. Luby, "Inheritance of Flower Color in *Dendranthema grandiflora* Tzvelev. (*Chrysanthemum morifolium* Ramat.) Using Cultivars and Inbreds. II. Vacuole Pigmentation", *Euphytica,* 42 (1989): 297-305, Kluwer Academic Publishers, The Netherlands.

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Yellow Tara particularly characterized by its flat capitulum form; anemone capitulum type; yellow ray floret color; diameter across face of capitulum of up to 7.5 cm at maturity, with diameter of anemone cushion of up to 3 cm when grown as a pinched spray pot mum; uniform eight week photoperiodic flowering response to short days; medium plant height when grown as a pinched pot mum; and spreading and prolific branching pattern.

3 Drawing Sheets

The present invention comprises a new and distinct cultivar of Chrysanthemum, botanically known as *Dendranthema grandiflora,* and referred to by the cultivar name Yellow Tara.

Yellow Tara, identified as 83-436A26, is a product of a mutation induction program which had the objective of creating new Chrysanthemum cultivars that would expand the color range of an existing cultivar while retaining all other traits.

Yellow Tara was discovered and selected by Cornelis P. VandenBerg on Dec. 30, 1986 in a controlled environment in Salinas, Calif. as one flowering plant within a flowring block established as rooted cuttings from stock plants which had been exposed as unrooted cuttings to an X-ray source of 1750 rads. The irradiated parent was the cultivar identified as Tara, disclosed in U.S. Plant Pat. No. 6,313.

The first act of asexual reproduction of Yellow Tara was accomplished when vegetative cuttings were taken from the initial selection in March of 1987 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Yellow Tara are firmly fixed and are retained through successive generations of asexual reproduction.

Yellow Tara has not been observed under all possible environmental conditions. The phenotype may vary significantly with variations in environment such as temperature, light intensity and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Yellow Tara, which, in combination, distinguish this Chrysanthemum as a new and distinct cultivar:

1. Flat capitulum form.
2. Anemone capitulum type.
3. Yellow ray floret color.
4. Diameter across face of capitulum up to 7.5 cm at maturity, with a diameter of anemone cushion of up to 3 cm, when grown as a pinched spray pot mum.

5. Uniform eight week photoperiodic flowering response to short days.

6. Medium plant height, requiring 0 to 7 long days after pinch prior to short days and 1 application of 2500 ppm B-9 SP to attain a flowered plant height of 25 to 35 cm for year-round flowrings when grown as a pinched pot mum in a 15 cm pot.

7. Branching pattern is spreading and prolific.

The accompanying photographic drawings show typical inflorescence and leaf characteristics of Yellow Tara, with the colors being as nearly true as possible with illustrations of this type. Sheet 1 is a color photograph of Yellow Tara grown as a pinched spray pot mum. Sheet 2 is a black and white photograph of three views of the inflorescence of Yellow Tara. Sheet 3 is a black and white photograph showing the upper and under sides of the leaves of Yellow Tara at three stages of development (mature, intermediate and immature).

Of the commercial cultivars known to the inventor, the most similar in comparison to Yellow Tara is the parent cultivar Tara. All traits of Yellow Tara are similar to those of Tara, except the color of ray florets. Yellow Tara has a bright yellow ray floret color, while the color of Tara is pure white.

In the following description color references are made to The Royal Horticultural Society Color Chart. The color values were determined on plant material grown as a pinched spray pot mum in Salinas, Calif. on Mar. 31, 1989.

Classification:

*Botanical.*—*Dendranthema grandiflora* cv Yellow Tara.

*Commercial.*—Anemone spray pot mum.

INFLORESCENCE

A. Capitulum:

*Form.*—Flat.

*Type.*—Anemone.

*Diameter across face.*—Up to 7.5 cm at maturity.

*Diameter of anemone cushion.*—Up to 3 cm.

B. Corolla of ray florets:

*Color (general tonality from a distance of three meters).*—Yellow.

*Color (upper surface).*—5B.

*Color (under surface).*—5C to 5D.

*Shape.*—Slightly concave, straight, oblong.

C. Corolla of disc florets (Anemone cushion):

*Color (mature).*—9B.

*Color (immature).*—6A tinged with 144B.

D. Reproductive organs:

*Androecium.*—Present on disc florets only; scant pollen.

*Gynoecium.*—Present on both ray and disc florets.

PLANT

A. General appearance:

*Height.*—Medium; 25 to 35 cm as a pinched spray pot mum with 0 to 7 long days after pinch prior to short days and 1 application of 2500 ppm B-9 SP.

*Branching pattern.*—Spreading and prolific.

B. Foliage:

*Color (upper surface).*—147A.

*Color (under surface).*—147B.

*Shape.*—Lobed and serrated.

I claim:

1. A new and distinct Chrysanthemum plant named Yellow Tara, as described and illustrated.

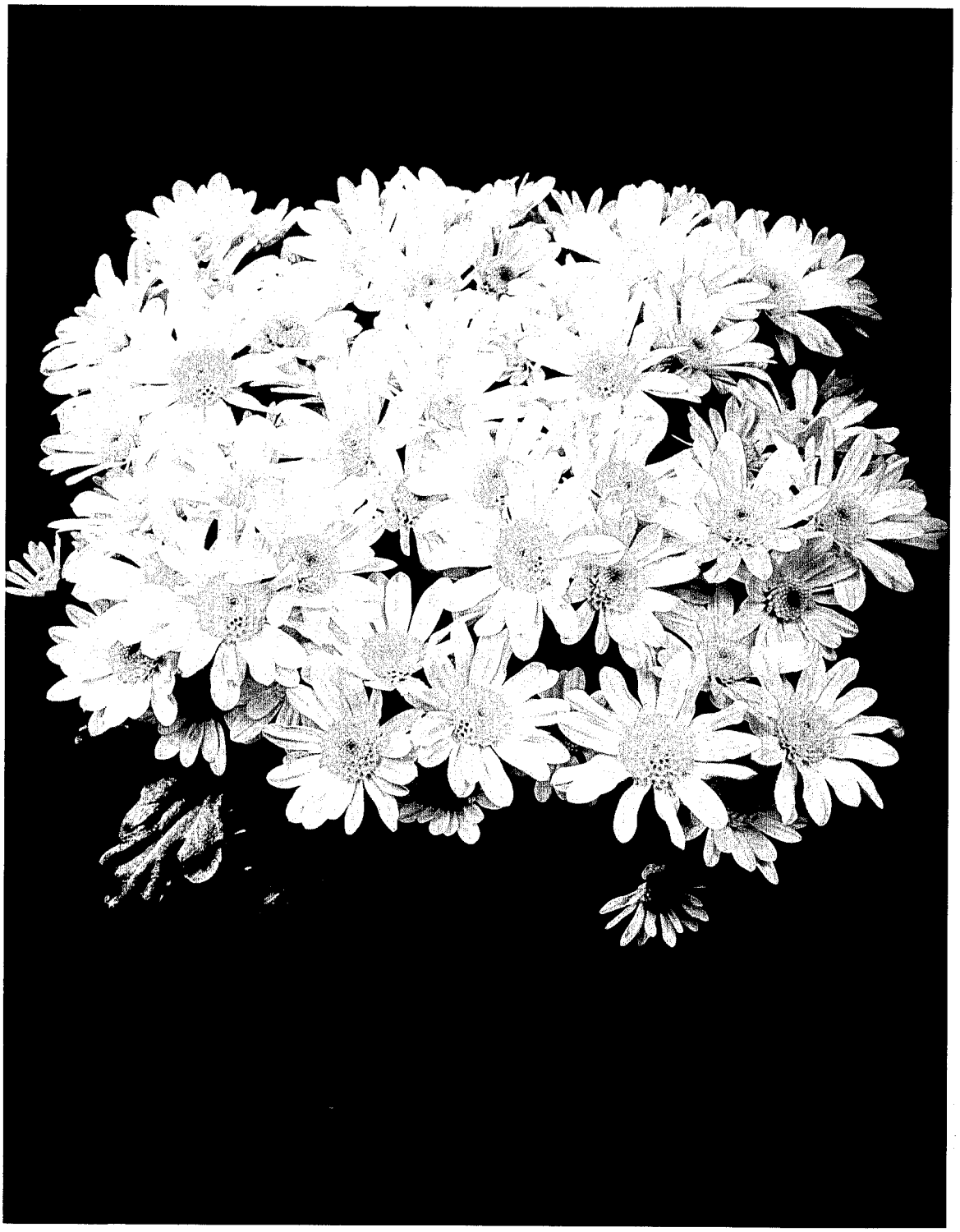

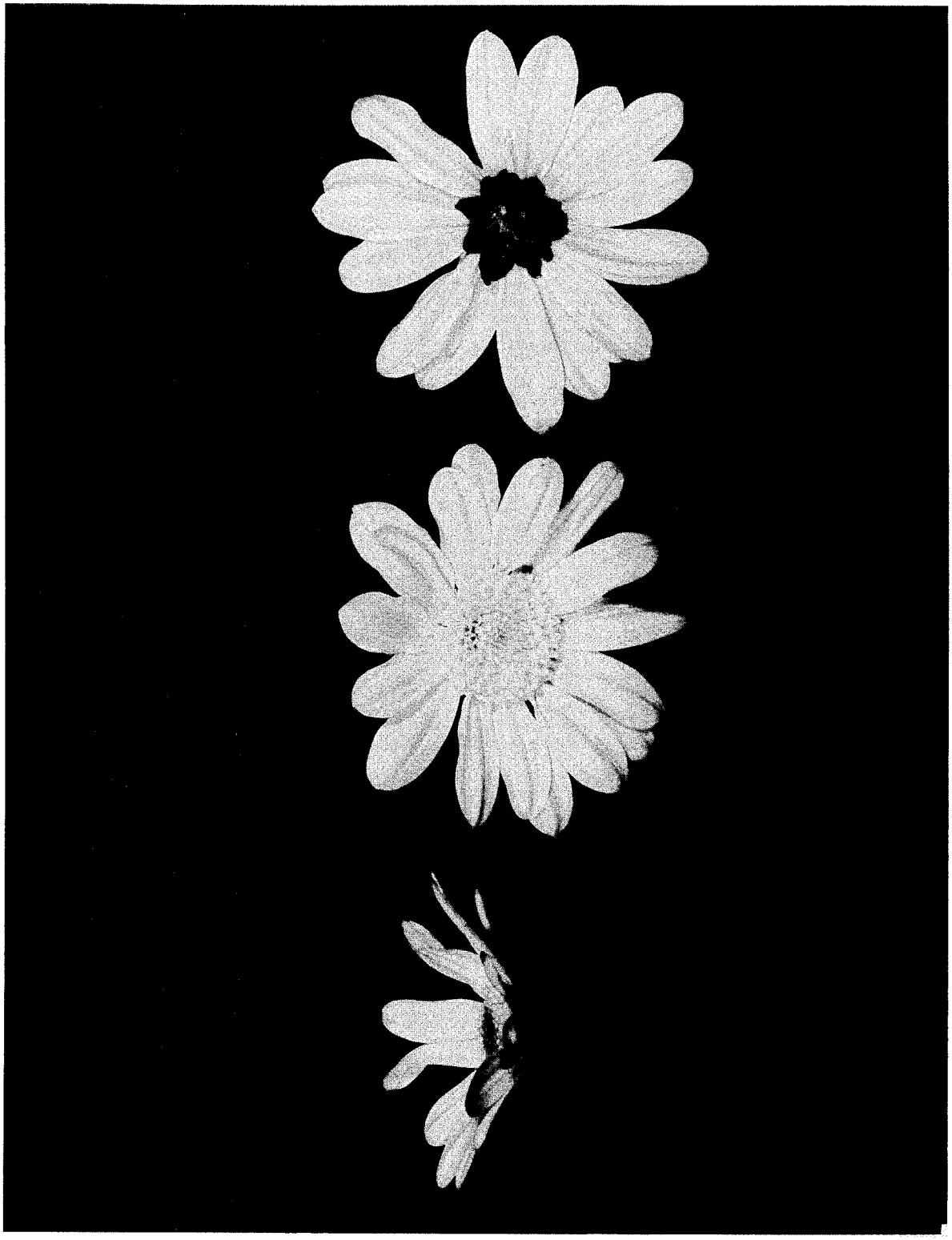

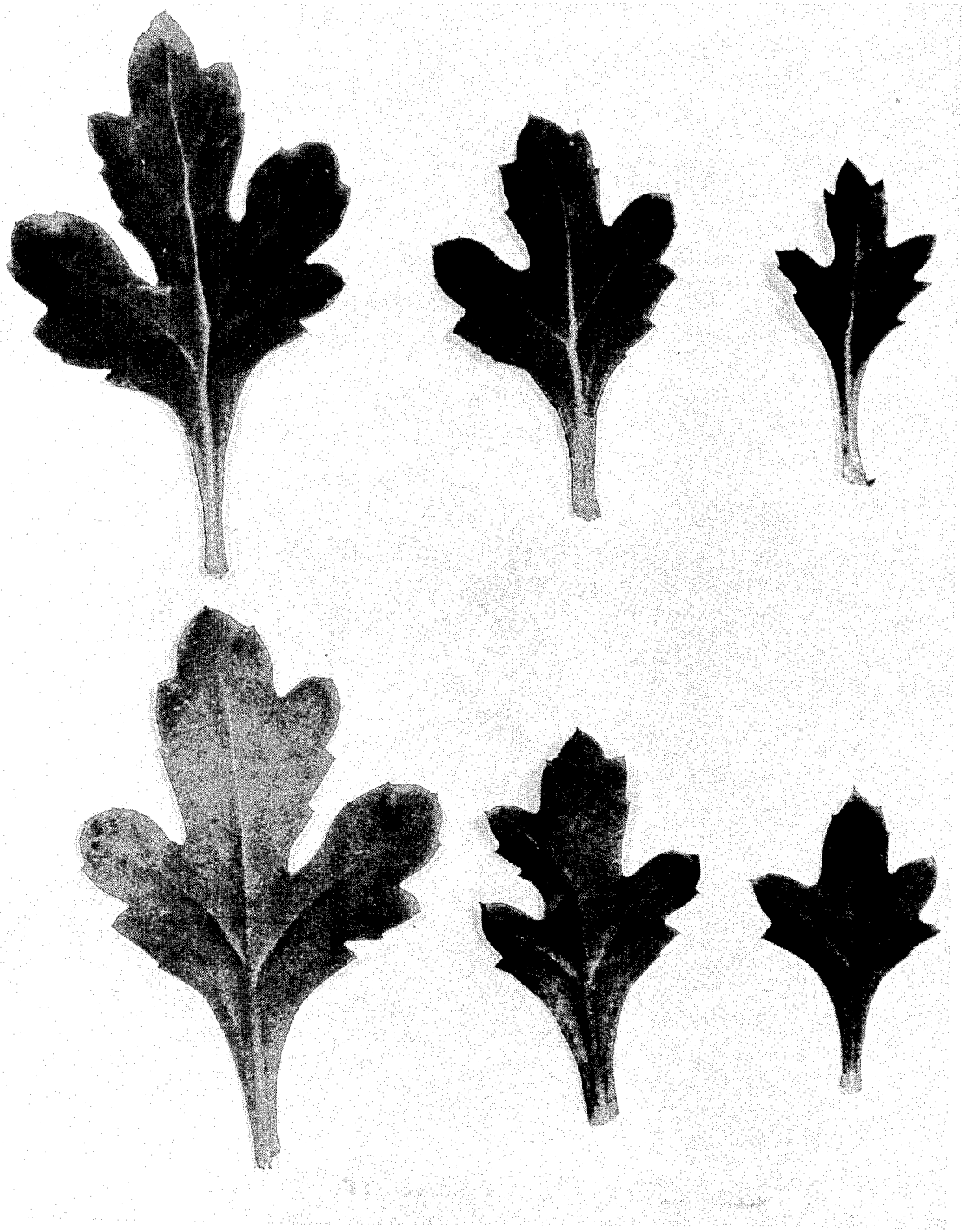

* * * * *